United States Patent [19]

Puumalainen et al.

[11] Patent Number: 4,812,665
[45] Date of Patent: Mar. 14, 1989

[54] METHOD AND APPARATUS FOR MEASURING OF HUMIDITY

[75] Inventors: Pertti Puumalainen; Reijo Kuusela, both of Kuopio, Finland

[73] Assignee: Roibox OY, Kuopio, Finland

[21] Appl. No.: 26,219

[22] Filed: Mar. 16, 1987

[51] Int. Cl.⁴ .......................... G01J 3/50; G01N 21/27
[52] U.S. Cl. .................................. 250/571; 250/338.1; 250/341
[58] Field of Search ............... 250/559, 571, 338, 339, 250/341; 356/402, 419

[56] References Cited

U.S. PATENT DOCUMENTS

| | | | |
|---|---|---|---|
| 3,641,349 | 2/1972 | Dahlin . | |
| 3,675,019 | 7/1972 | Hill et al. . | |
| 3,965,356 | 6/1976 | Howarth | 250/339 |
| 4,006,358 | 2/1977 | Howarth | 250/339 |
| 4,052,615 | 10/1977 | Cho | 250/341 |
| 4,171,918 | 10/1979 | Mactaggart | 250/339 |

Primary Examiner—Edward P. Westin
Attorney, Agent, or Firm—Cushman, Darby & Cushman

[57] ABSTRACT

The object of the invention is a method for measuring humidity in material to be produced in the form of a web, particularly paper and carton material. According to the method, a chopper in part cuts infrared light brought on the other side of the web through an opal glass window from an infrared source. The radiation is measured in an analysis part placed adjacent a second opal glass window. Humidity in the web is measured by measurement of the measuring and reference wavelengths; intensities with a measuring analyzer and a reference analyzer and simultaneously adjusting the viewing angles of the analyzers in such a manner, that when the position of the material web between the opal windows is changed, the same value for the humidity is obtained. The wavelengths between the measuring and reference channels have been chosen so that they are as near as possible to each other.

6 Claims, 2 Drawing Sheets

METHOD AND APPARATUS FOR MEASURING OF HUMIDITY

BACKGROUND OF THE INVENTION

1. Field of the Invention

The present invention relates to a method and apparatus for measuring the humidity that is present in materials produced in the form of a web. More particularly, the present invention relates to the monitoring of humidity in paper type webs during the manufacturing process.

2. Description of the Prior Art

Different types of infrared hygrometers are known in the prior art, and most of these are based on the absorption of two or more wavelengths of light or radiation in a water containing material.

The transmission meters used for the measuring of the humidity in materials produced in form of a web, in particular paper or carton, can be divided into two different groups. The first group is characterized by meters which contain so-called integrating balls, into which measuring and reference beams are applied sequentially, arranged in periods, and analyzed by one detecting instrument. In the devices of the second group, the radiation is scattered between two mirrors, into which interspace the web to be examined may be placed, creating an infrared radiation sample, the intensities of the measured and reference wavelengths of which may be simultaneously analyzed.

The aforementioned methods are connected with certain disadvantages. In those methods the intensities of the measuring and reference wavelengths passed through the material to be examined are measured against each other, and as a result the moisture content value achieved becomes very much dependent on the square unit weight of the material, the filling substances, the degree of beating of the fibers etc. factors. An additional weakness of these methods and meters is that it provides only a narrow range of measuring, because if the humidity exceeds 15 per cent, the meters are no longer dependable and give false measuring readings for a wet (moisture percentage 30-50 per cent) material. Further it is not possible to measure moisture content from materials having a high square unit weight, such as thick cartons. Often materials exceeding 200 g/m$^2$ in their square unit weight are difficult to measure.

When applying the present methods and devices the position of the material web in the measuring interspace has an influence on the measuring result. The hygrometer and the material to be measured constitute an optical entirety, which is a total of several partial factors. The material web is generally not transparent, but it acts as a kind of a light diffuser. The light coming from the light source is not isotropic or depending on the optics applied in the middle of the light beam a greater illumination than on its edges is to be observed. In the measuring of humidity, different wavelengths are used in the water and reference channels. Because the scattering phenomenon of the light is depending on the wavelength, the disintegrating materials and the material web scatter these different wavelengths in different ways. In practice the optical signals detected by the analyzers change due to the factors mentioned above when the position of the material web is changed in the measuring interspace.

SUMMARY OF THE INVENTION

The purpose of the invention is to bring forth a method for measuring humidity, by which it becomes possible to measure the moisture content ranges of 0-100 per cent for all paper and carton qualities or corresponding materials materials irrespective of the material, and by which the dependence of the results of the square unit weight of the material, the filling substance content and/or the beating degree is very small compared with the presently known methods. Further it is an object of the invention to bring about a method, by which a quick, dependable reading is achieved independent from the position of the material web in the measuring interspace.

According to the invention the infrared radiation is measured from one of two windows made of light disintegrating material which are placed between the material web and the analyzers, and at the same time adjusting the analyzers in such an angle in respect to the window, that in the measuring of the humidity the same value is achieved independent of the material web's position between the windows. With this method, the light is diffused extremely efficiently by means of the windows made of disintegrating material, which are favourably opal windows or the like.

The importance and function of the position dependence adjustment becomes quite clear, if we assume, that the opal windows (or windows made of corresponding material) and the material web between them constitute as an entirety a light diffuser, the light disintegrating properties of which are not ideal and, that the light reflecting properties change when the position of the material web in the measuring interspace changes. This phenomenon has been illustrated in FIG. 1, where the curve (a) describes the light reflecting properties of this entirety when the material web is located in the one of the extreme edges and curve (b) describes the light reflecting properties when the material web is located in the opposite extreme edge. The order of the curves is of no significance in practice. The vertical lines crossing the curves present the signals detected by the analyzers. As the positions of the vertical lines can be chosen freely, or in practice, the angles of the analyzers are adjusted in respect of the window, such angles for the analyzers are found, that the relative change of the measured signals is the same when the material web moves from one extreme edge to the other. In case the measurings are performed in accordance with the angles presented with the uninterrupted lines, the dependence of the position is to be seen in the results and the measuring result is not correct. When using the detection angles presented by the broken lines an optimum adjustment is achieved, and the measuring results do not depend on the position of the material web between the windows.

BRIEF DESCRIPTION OF THE DRAWINGS

In the following the invention is presented more in detail by referring to the attached drawing is, in which.

DETAILED DESCRIPTION OF THE PREFERRED EMBODIMENT

Figure 2:
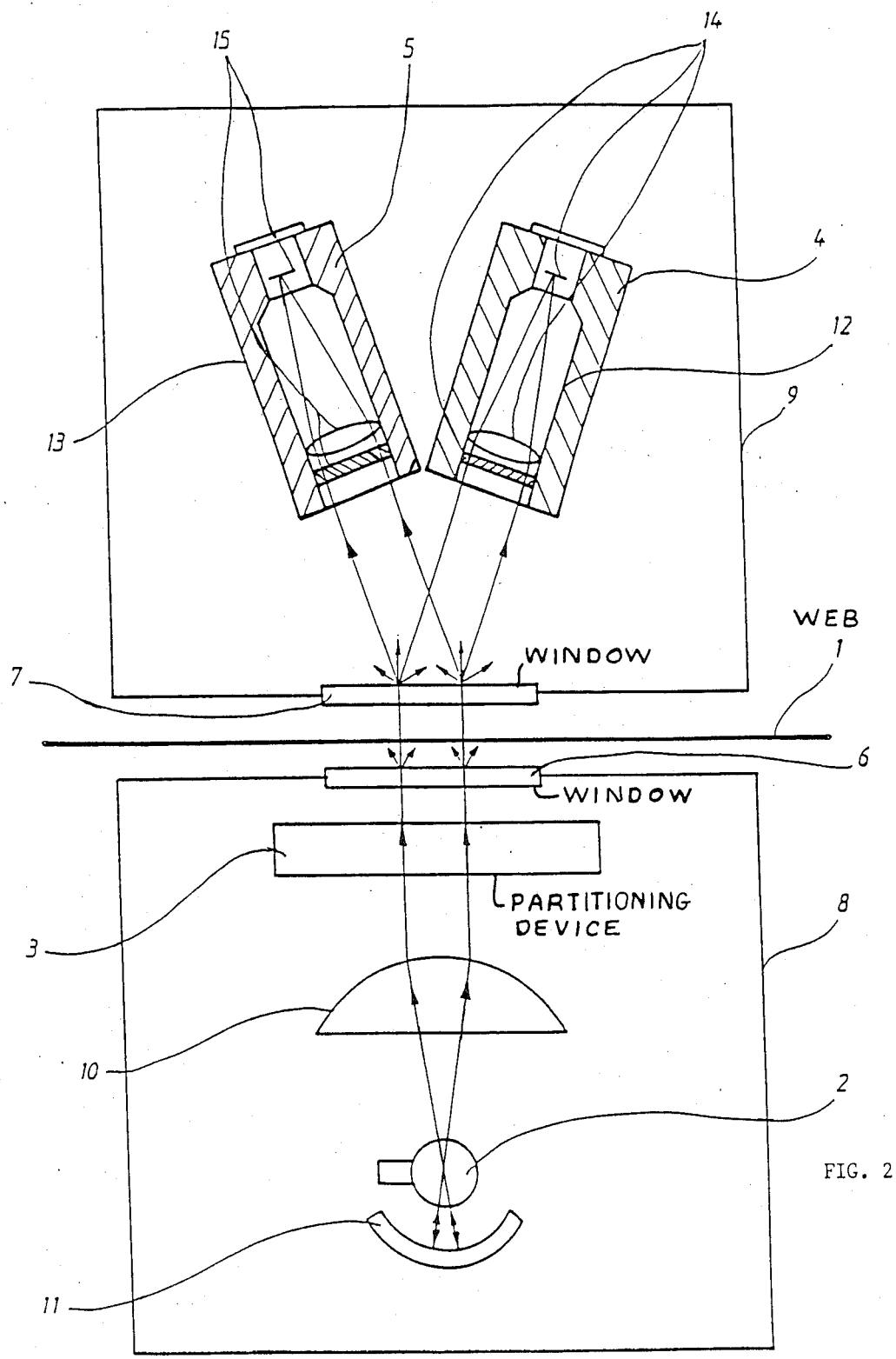
FIG. 2 presents one device for application of the method in accordance with the invention in cross-section.

Referring to FIG. 2, on one side of the material web is placed the infrared source part 8 and on the opposite side of the material web is placed the analyzer part 9. To the infrared source part belong the infrared source 2, and between the infrared source and the material web is placed a partitioning device 3, the so-called chopper, for cutting the radiation into parts. Near the infrared source is placed a lens 10 and mirror 11 for concentrating the radiation into the chopper, and between the material web and the chopper 3 is placed of a window made of light disintegrating material, favourably an opal window 6 or corresponding, for diffusing of the infrared radiation. The chopper is arranged to cut the radiation into parts e.g. with the help of an oscillation of a certain frequency, slots or similar. To the analyzer part 9 belong a measuring analyzer 4 and a reference analyzer 5 as well as light disintegrating material window between the analyzers and the material web, favourably an opal window 7. To the analyzers belong the directive tubes 12, 13 for collimation of the radiation into the analyzers and the filter, lens, and detector combinations 14, 15. The analyzers are similar to each other in their structure, the only difference being, that in the measuring analyzer the filters allow the measuring wavelength to pass to the detector, which is above the water absorption wavelength, and in the reference analyzer the filters allow the reference wavelength to pass to the detector, which is favourably next to the water absorption wavelength immediately.

The analyzers are arranged so as to be separate and adjustable in regard to each other and/or the opal window 7, for instance by connecting them articulated to the analyzer part or in some other known way. The analyzers are adjustable either together or separately for changing of the angle between themselves and/or the angle between them and the opal window, but in such a way, that they always view mainly the same area of the opal glass window surface.

The alignment and the determination of the moisture content by using the method in accordance with the present invention proceeds in the following way:

The interspace between the infrared source part 8 and the analyzer part 9, where the material web is passing during the production and the measuring, is adjusted to the desired value. The radiation transmitted from the infrared source is pointed with the help of the mirror and the lens through the chopper to the opal glass window, into which an efficient luminous beam is obtained. The opal window scatters the light in every direction and part of the light comes to the opal window of the analyzer part. During the calibration the material web is not yet placed in the interspace. The opal window scatters the light efficiently and part of the light is detected on the analyzers. In this way the comparison values are obtained, because the material web is not yet between the infrared part and the analyzer part.

Further in the calibration the sample material is placed between the parts and the viewing angle of the analyzers to the opal window is adjusted in such a way, that always the same humidity value is obtained, although the sample would be in its most extreme values, against either the opal window 6 or 7. The device can be calibrated for the whole production of a machine, but if wished the viewing angles can also be changed.

A meter reading comparable with the humidity value of the sample material may then be obtained by calculation taking advantage of the starting values, which were measured when nothing is between the parts, by bringing the absorption of the measuring beam into relation with the absorption of the reference beam. Earlier only the relation of the intensities in the measuring and reference beams passed-through had been calculated. When the processes of calculation in this manner have been made taking advantage of this new method and the wavelengths are from the point of view of the other materials except for the water nearly the same, the water quantity by the passed light way distance can be determined, whereat the square unit weight and other errors causing factors grow considerably smaller.

In some other applications of the method the material web is examined with more than two analyzers or more than twice with, an adjustable viewing angle equipped analyzers. Hereby the measuring result is obtained still more accurately.

Figure 1:
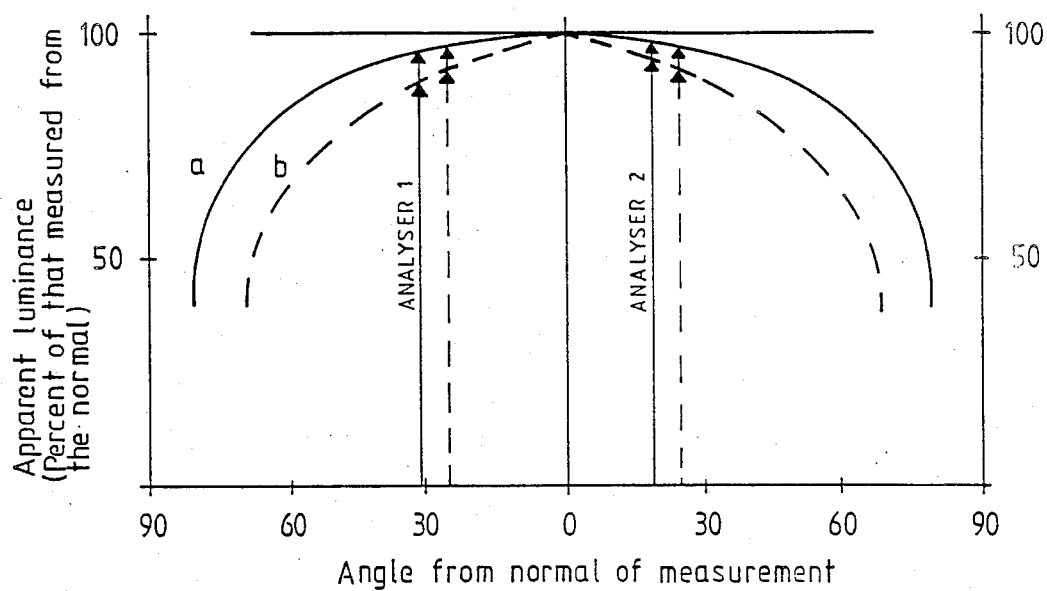
FIG. 1 depicts the light reflecting properties as above described versus angle of measurement.
Figure 3:
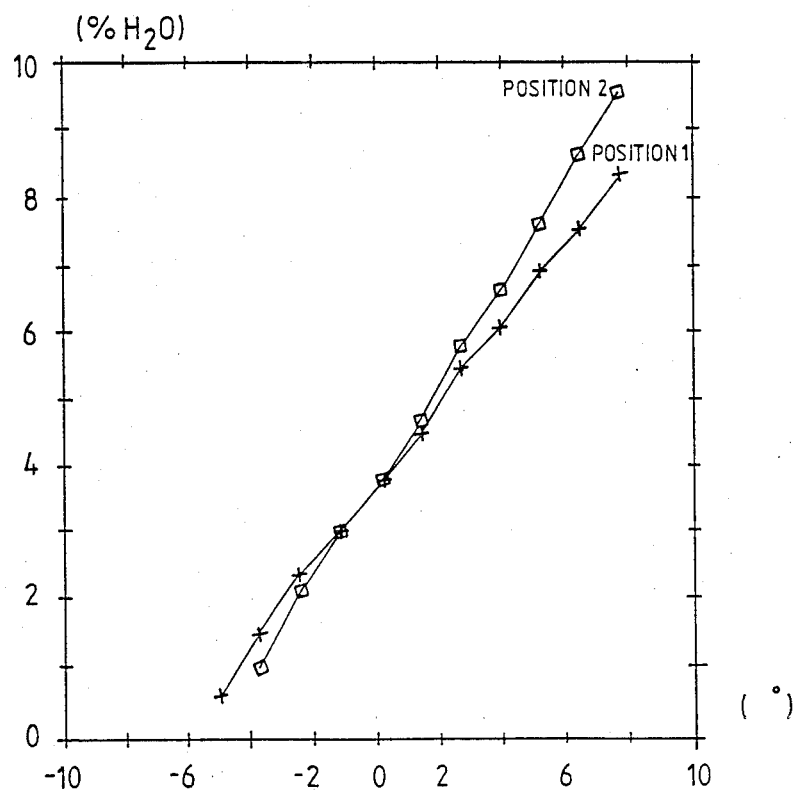
FIG. 3 presents the influence of the detection angle on the dependence of the position of the material web.

The influence of the adjustment of the analyzer angle has been investigated and in the following table the measuring results have been presented, from which appear the influence of the angle adjustment ton the dependence of the position on the humidity results. In FIG. 3 the corresponding results have been presented in form of curves.

| Angle (°) | Moisture percentage | |
|---|---|---|
| | Position 1 | Position 2 |
| −5.2 | 0,598 | −0.317 |
| −3.9 | 1.512 | 1.062 |
| −2.6 | 2.351 | 2.112 |
| −1.3 | 3.063 | 3.023 |
| 0.0 | 3.847 | 3.836 |
| 1.3 | 4.561 | 4.737 |
| 2.6 | 5.542 | 5.862 |
| 3.9 | 6.149 | 6.707 |
| 5.2 | 7.006 | 6.699 |
| 6.5 | 7.594 | 8.689 |
| 7.8 | 8.456 | 9.613 |

In this sample, the water and reference analyzers were connected to each other family, whereby the angle of both in respect of the opal glass was adjusted to the same extent. The material web to be measured was a 80 g/sq m white offsetpaper, which had been air-conditioned in room air to a balanced humidity, which was about 5 per cent.

The humidity was measured from the paper as a function of the analyzers' angle with each angle firstly the paper being in a device in accordance with FIG. 2 in its extreme position on the side of the window 7 (the measuring results in Position 1) and immediately thereafter the humidity of the paper was measured when it was at its extreme position on the side of the window 6 (measuring results in Position 2), the distance between the two extreme positions being in this application about 15 mm.

From the measuring results can be observed, that a certain optimum angle exists, measured from which the humidity result is not depending on the position of the paper in the measuring interspace. At this angle the humidity curves measured from one extreme position of the measuring inter space to the other one as a function of the angle cross each other as presented on FIG. 3. the measured humidity values change also to their figure values as a function of the angle, but this is without any significance because the hygrometer is calibrated only after that the dependence of the position has been adjusted away.

By using the method in accordance with the invention also very thick carton qualities can be measured, even cellulose sheets, the square unit weight of which can be 1000 g/q m. In several measurings it has been observed, that humidity values can be measured accurately with the moisture percentage being 0-100 per cent. Likewise it has been observed, that for instance the doubling of the square unit weight does no affect the result more than less than 0.2 per cent units.

The invention is not limited to the presented favourable applications, but it can very within the frames of the patent claims.

We claim:

1. A method for measuring humidity in a web material comprising:
    (a) detecting the intensity of a reference wavelength from an infrared source that has passed through a pair of lightdiffusing windows which define a space therebetween with a reference analyzer;
    (b) positioning the web material within the space between the windows;
    (c) detecting the intensity of a measuring wavelength that has passed through the web and the two windows with a measuring analyzer;
    (d) changing the angular positions of the reference analyzer and the measuring analyzer; and
    (e) repeating steps (a)-(c) until the measurements of the two analyzers are substantially the same, whereby the humidity of the web may be accurately calculated.

2. A method according to claim 7, wherein the reference analyzer and measuring analyzer always examine the same area on the window proximate to them independent of their angle of adjustment.

3. A method according to claim 7, wherein the windows are formed of opal.

4. Method in accordance with claim 1 characterized in, that the measuring and reference wavelengths are as near as possible to each other, whereby the humidity content of the web is calculated by means of known calibrating samples.

5. An apparatus for measuring humidity in web material, comprising:
    a pair of light-diffusing windows defining a space therebetween;
    infrared source means positioned to a first side of said windows;
    reference analyzer means positioned to a second side of said windows for measuring the intensity of light from said source means passing through the windows when no web is therebetween; and
    measurement analyzer means positioned to said second side of said windows for measuring the intensity of light from said source means that has passed through said windows and a web therebetween, said reference analyzer means and said measurement analyzer means being angularly adjustable with respect to said windows.

6. Apparatus according to claim 5, wherein said windows are formed of opal.

* * * * *